US012697433B2

(12) United States Patent
Varma Kunaparaju et al.

(10) Patent No.: US 12,697,433 B2
(45) Date of Patent: Aug. 4, 2026

(54) DISPLACEMENT PUMP MECHANISM WITH FRANGIBLE RESERVOIR, MEDICAMENT DELIVERY SYSTEM, PATCH PUMP AND MEDICAMENT DELIVERY DEVICE

(71) Applicant: Becton, Dickinson and Company, Franklin Lakes, NJ (US)

(72) Inventors: Nitish Kumar Varma Kunaparaju, Andover, MA (US); Mark Wood, Sterling, MA (US); Dan Yasevac, San Diego, CA (US); Khodabakhsh Saeedi, Natick, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 652 days.

(21) Appl. No.: 18/019,354

(22) PCT Filed: Aug. 5, 2021

(86) PCT No.: PCT/US2021/044607
§ 371 (c)(1),
(2) Date: Feb. 2, 2023

(87) PCT Pub. No.: WO2022/031888
PCT Pub. Date: Feb. 10, 2022

(65) Prior Publication Data
US 2023/0285663 A1      Sep. 14, 2023

Related U.S. Application Data

(60) Provisional application No. 63/062,158, filed on Aug. 6, 2020.

(51) Int. Cl.
*A61M 5/142* (2006.01)
*A61M 5/315* (2006.01)

(52) U.S. Cl.
CPC .... *A61M 5/14248* (2013.01); *A61M 5/31511* (2013.01); *A61M 2005/14252* (2013.01)

(58) Field of Classification Search
CPC .......... A61M 5/14248; A61M 5/31511; A61M 2005/14252; A61M 5/1452; A61M 5/3129; A61M 2005/31518
See application file for complete search history.

(56) References Cited

U.S. PATENT DOCUMENTS 6,800,071 B1    10/2004   McConnell et al.
10,350,358 B2    7/2019   Schenker et al.
(Continued)

FOREIGN PATENT DOCUMENTS

JP        H09-512472 A      12/1997
JP        2002-528676 A      9/2002
(Continued)

*Primary Examiner* — James D Ponton
(74) *Attorney, Agent, or Firm* — Dickinson Wright PLLC

(57) ABSTRACT

Medication delivery system including a container, reservoir, or chamber for medium or fluid, and a mechanism or driving components configurable outside of medium or fluid chamber for advancing a plunger to dispense medium or fluid. The system can include syringe-style drug container, reservoir, or chamber, containing medium or fluid dispensable by advancing plunger disposed inside the container, where the container includes a sliceable portion and where a cutter or slicer is configurable on plunger holder or pusher behind plunger such that cutter cuts through sliceable portion of container as plunger is advanced dispensing medium out of container. The present disclosure is further directed to a patch pump comprising the system as described above. The present disclosure is further directed to a medicament delivery device comprising the system as described above.

18 Claims, 15 Drawing Sheets

(56) References Cited

U.S. PATENT DOCUMENTS

| | | | | |
|---|---|---|---|---|
| 2004/0059300 A1* | 3/2004 | Kosinski | ............. | A61M 5/5013 |
| | | | | 604/213 |
| 2008/0171969 A1 | 7/2008 | Byrne et al. | | |
| 2010/0249706 A1 | 9/2010 | Clemente | | |
| 2012/0330245 A1 | 12/2012 | Mudd | | |
| 2014/0214001 A1 | 7/2014 | Mortazavi | | |
| 2016/0089491 A1* | 3/2016 | Smith | ................. | A61M 5/1452 |
| | | | | 604/154 |
| 2020/0399046 A1* | 12/2020 | Luke | .................... | B41J 2/17553 |

FOREIGN PATENT DOCUMENTS

| | | | |
|---|---|---|---|
| JP | 2009-508638 A | 3/2009 |
| JP | 2010-501277 A | 1/2010 |
| WO | WO-2019226145 A1 | 11/2019 |

* cited by examiner

308

704

702

408

308

704

408

702

DISPLACEMENT PUMP MECHANISM WITH FRANGIBLE RESERVOIR, MEDICAMENT DELIVERY SYSTEM, PATCH PUMP AND MEDICAMENT DELIVERY DEVICE

CROSS-REFERENCE TO RELATED APPLICATIONS

This application claim priority under 35 USC § 119 (e) from U.S. Provisional Patent Applications No. 63/062,158 filed Aug. 6, 2020, the content of which (including all attachments filed therewith) is hereby incorporated by reference in its entirety.

FIELD OF THE DISCLOSURE

Generally, exemplary embodiments of the present disclosure relate to the fields of medication delivery devices. More specifically, exemplary embodiments of the present disclosure relate to medication delivery devices where a stopper or plunger is advanced through a reservoir to dispense medication from the reservoir.

BACKGROUND

In the example of medical applications, a patch pump is an integrated device that facilitates infusion therapy for diabetic patients. A patch pump combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may be configured to include wireless communication with a separate controller device, while others are completely self-contained. Such devices are replaced on a frequent basis, such as every three days, particularly when the insulin reservoir is exhausted.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall size of the patch pump. Conventional patch pumps or a syringe-type devices typically include a driving mechanism with a single advancing lead screw inside medium or fluid reservoir or chamber to push, advance, or otherwise apply force on the plunger in order to dispense the medium or fluid out of the chamber. In order to minimize the size of the patch pump, its constituent parts, such as driving mechanisms, should be reduced as much as possible without compromising the accuracy and reliability of device or its feature set.

SUMMARY OF THE DISCLOSURE

An exemplary embodiment provides a system comprising: a container for a medium; a plunger disposed in the container; and a mechanism for advancing the plunger distally to dispense the medium from the container, where the mechanism is disposed outside of the container.

An exemplary implementation of any exemplary embodiment, provides for the container to include a sliceable portion extending essentially linearly from a proximal portion to a distal portion of the container, the plunger including a distal surface disposed inside the container, the distal surface facing the medium inside the container, and the mechanism comprising: a pusher acting on the plunger; and a cutter configured with the pusher behind the plunger, the cutter configure to slice through the sliceable portion of the container as the plunger advances distally to dispense the medium out of the container.

Another exemplary implementation of any exemplary embodiment, provides for the mechanism to further comprise a lead screw disposed outside of the container and axially fixed with respect to the container, the lead screw being in lateral engagement with the pusher.

Yet another exemplary implementation of any exemplary embodiment, provides for the mechanism further comprising a driver rotating the lead screw to advance the plunger.

Still another exemplary implementation of any exemplary embodiment, provides for the mechanism comprising at least one gear transferring rotation of the driver to the lead screw, the gear being disposed at a proximal end of the container, the medium being dispensed at a distal end of the container.

Yet further exemplary implementation of any exemplary embodiment, provides for system further comprising a nut in threaded communication with the lead screw and connected with at least one of the pusher and the cutter, the nut moving axially relative to the housing due to rotational movement of the lead screw, thereby advancing the pusher and the cutter.

Another exemplary implementation of any exemplary embodiment, provides for the cutter comprising a blade, the blade laterally connecting the pusher and the nut, the blade comprising a slicing edge that slices through the sliceable portion of the container.

A further exemplary implementation of any exemplary embodiment, provides for the container comprising an end-cap disposed at a distal end portion of the container, the endcap comprising at least one of an outlet for dispensing the medium and an inlet for filling the container.

Still further exemplary implementation of any exemplary embodiment, provides for the system where the container comprises: a soft inner layer accommodating the medium; a rigid outer layer; and the sliceable portion comprising a cutting channel exposing a portion of the soft inner layer and extending linearly between the proximal end and distal end of the container.

According to an exemplary implementation of any exemplary embodiment, provides for a cutting channel configured to accommodate the cutter when the plunger advances to dispense the medium, the cutter advancing through the channel slicing the exposed portion of the soft inner layer.

According to an exemplary implementation of any exemplary embodiment, a soft inner layer comprises an overmold inside a rigid outer layer.

According to an exemplary implementation of any exemplary embodiment, a soft inner layer is bonded inside a rigid outer layer.

Another exemplary implementation of any exemplary embodiment, provides for a container that is cylindrical having one of a circular or elliptical cross section.

Another exemplary implementation of any exemplary embodiment, provides for a system wherein the container is cylindrical having one of a circular or elliptical cross section, an outer wall of the inner layer extending parallel to an inner wall of the outer layer.

Another exemplary embodiment of the disclosure provides a patch pump comprising the system including any combination of disclosed configurations comprising: a container for a medium; a plunger disposed in the container; and a mechanism for advancing the plunger distally to dispense the medium from the container, where the mechanism is disposed outside of the container.

Yet another exemplary embodiment of the disclosure provide a medicament delivery device comprising the system including any combination of disclosed configurations comprising: a container for a medium; a plunger disposed in the container; and a mechanism for advancing the plunger distally to dispense the medium from the container, where the mechanism is disposed outside of the container.

Objects, advantages, and salient features of the disclosure will become apparent from the following detailed description, which, taken in conjunction with the annexed drawings, discloses exemplary embodiments, and non-limiting combinations of features, of the disclosure.

BRIEF DESCRIPTION OF THE DRAWINGS

Referring now to the drawings, wherein like reference numerals designate identical or corresponding parts throughout the several views, embodiments of the present disclosure are described as follows.

DETAILED DESCRIPTION OF EXEMPLARY EMBODIMENTS OF DISCLOSURE

Figure 1:
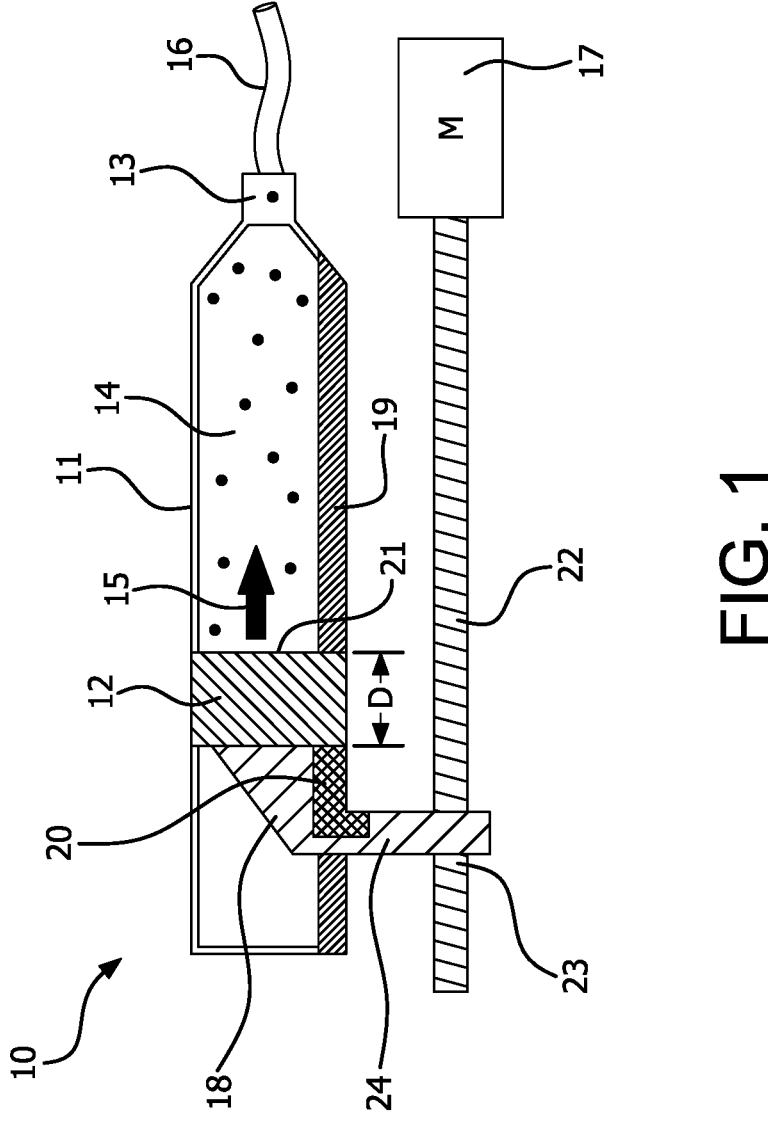
FIG. 1 diagrammatically illustrates a combination of system components according to exemplary embodiment of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

As would be readily appreciated by skilled artisans in the relevant art, while descriptive terms such as "medium", "medicament", "stopper", "plunger", "thread", "syringe", "motor", "bridge", "nut", "blade", "cutter", "slice", "sliceable", "gear", "sharp", "wall", "top", "side", "bottom," "upper," "lower," "proximal", "distal", "container", "reservoir", "chamber" and others are used throughout this specification to facilitate understanding, it is not intended to limit any components that can be used in combinations or individually to implement various aspects of the embodiments of the present disclosure.

Exemplary embodiments of the present disclosure provide system components that can facilitate a reduction in the overall size or footprint of a drug delivery device, such as a patch pump, by a configuration of a container, reservoir, or chamber for medium or fluid and a mechanism or driving components for advancing a plunger to dispense the medium or fluid, where the mechanism or driving components can be disposed outside of the fluid or medium chamber.

Exemplary implementations of embodiments of the present disclosure provide combinations of various feature of a frangible reservoir design and ratchet mechanism for operational sequencing.

According to exemplary embodiments of the present disclosure, a system includes a syringe-style drug container, reservoir, or chamber containing a medium or fluid which can be dispensed by advancing a plunger disposed inside the container, where container includes a sliceable portion, plunger includes a distal surface disposed inside the container facing, or in contact with, or proximal to, the medium inside the container, and a cutter or slicer is configured on a plunger holder or pusher behind plunger such that the cutter or slicer slices or cuts through the sliceable portion of the container as plunger is advanced to dispense the medium or fluid out of the container.

According to exemplary embodiments of the present disclosure, significant space savings can be achieved by utilizing exemplary implementations of a mechanical drive mechanism that resides fully outside of the syringe barrel and, for example, behind the moving plunger as provided in the present disclosure. Thus, for example, simplifying drug compatibility of the device.

In exemplary implementations of embodiments of the present disclosure, a mechanism comprises a screw pump with a frangible reservoir. Such a configuration can ensure high performance, for example by advantageously utilizing a screw pump type design which can facilitate high precision, while reducing the foot print compared to, for example, a conventional design of a single advancing lead screw inside the reservoir.

Further, in exemplary implementations of the embodiments of present disclosure, a frangible reservoir can be configured with a sliceable section and features which minimizes cutting force but at the same time do not allow pressure loss and crack propagation.

In yet further exemplary implementations of embodiments of the present disclosure, a blade's approach angle and thickness can be optimized to minimize the cutting and drag forces.

In yet further exemplary implementations of embodiments of the present disclosure, features of configuration including a frangible reservoir, a cutting blade, and a pusher can be optimized, for example, to constrain moment and transfer the force to displace the stopper.

FIG. 1 diagrammatically illustrates a general concept of a system 10 according to exemplary embodiments of the present disclosure including a syringe-style drug container 11 containing medium 14, which can be dispensed, via an appropriate optionally attached or integrally designed feature such as a needle or tubing 16, by advancing a plunger 12 disposed inside container 11 in direction 15 toward outlet 13 at a distal end of container 11. Container 11 includes a sliceable portion 19. Plunger 12 includes a distal surface 21 configured to be disposed inside container 11 facing, or in contact with, or proximal to, medium 14 inside container 11. A cutter or slicer, such as a blade 20, is configured on a plunger holder or pusher 18, which can be a separate structure or integral part of plunger 12, behind distal surface 21 of plunger 12 at a distance D from distal surface 21. Distance D can be arbitrary or optimally chosen based on required design factors. Blade 20 is configured to slice or cut through sliceable portion 19 as plunger 12 is advanced in direction 15.

Plunger system 10 includes a mechanism 17 outside of container 11 for advancing plunger 12 at least distally in direction 15, for example by driving a rotatable rod 22 in threaded communication 23 with a threaded cutter or bridge 24 which mechanically connects plunger holder or pusher 18 a driver 17. In an exemplary implementation, bridge 24 can be configured to include, or itself be at least a part of cutter or blade 20. All of the components aside from a portion of pusher 18 are located outside of container 11.

Figure 2A:
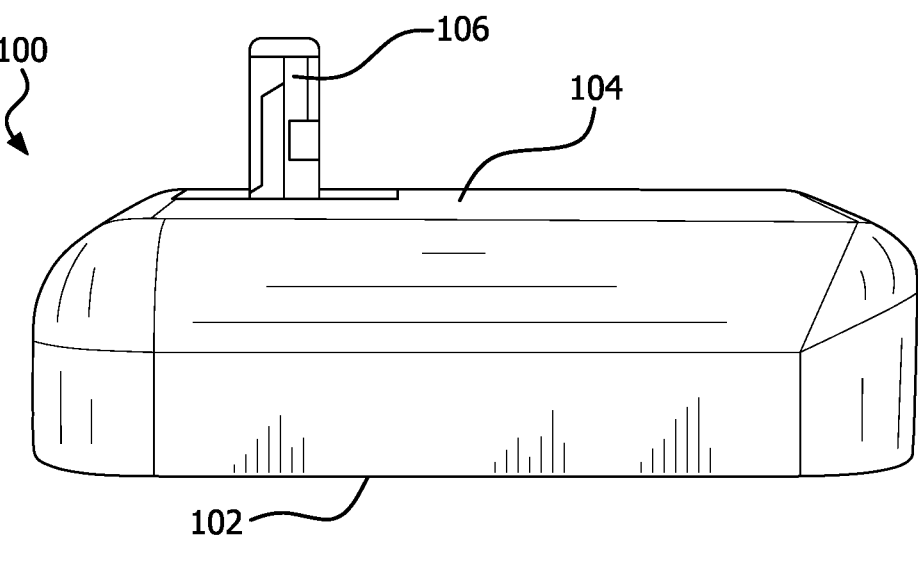
FIGS. 2A and 2B are examples of perspective views of an exterior of a device according to exemplary embodiment of the present disclosure.
Figure 2B:
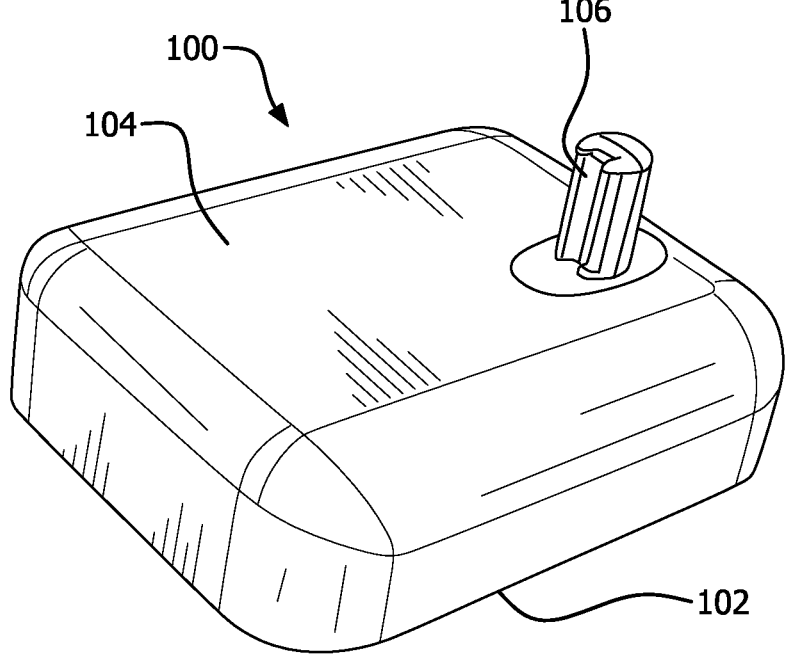

Referring to FIGS. 2A-6B, exemplary embodiments of the present disclosure can be applied to a pump concept, such as for example a wearable disposable patch pump 100 configured to include a base 102, outer housing 104, and an insertion mechanism 106, as shown in perspective views of FIGS. 2A and 2B. FIG. 3A is a perspective view of pump 100 without the outer housing or cover 104, and shows at least some of the various components that can be configured on base 102 of a pump 100 according to an exemplary implementation of the embodiments of the preset disclosure. Such components include a pumping mechanism 300 behind the pusher 302 and stopper or the plunger 304 of a syringe-style drug container 306 (having a distal end or portion 307 and a proximal end or portion 309) configured with a sliceable reservoir 308 to dispense medium. Examples of configurations of a pumping mechanism and syringe-style drug container with a sliceable reservoir, according to exemplary implementations of the present disclosure, are described in more detail below.

Figure 3A:
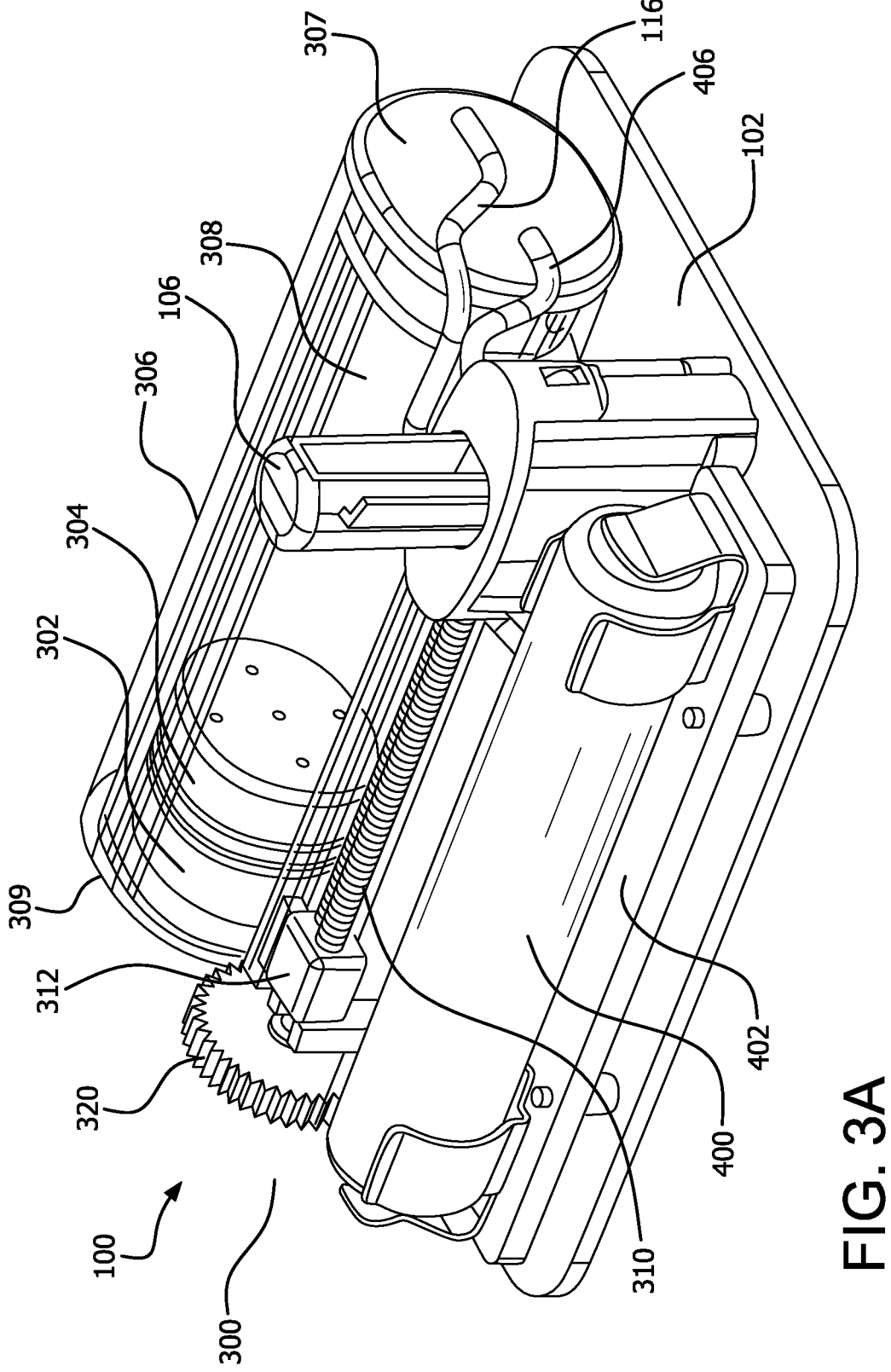
FIGS. 3A and 3B are examples of perspective views of components of a device according to exemplary embodiment of the present disclosure.
Figure 3B:
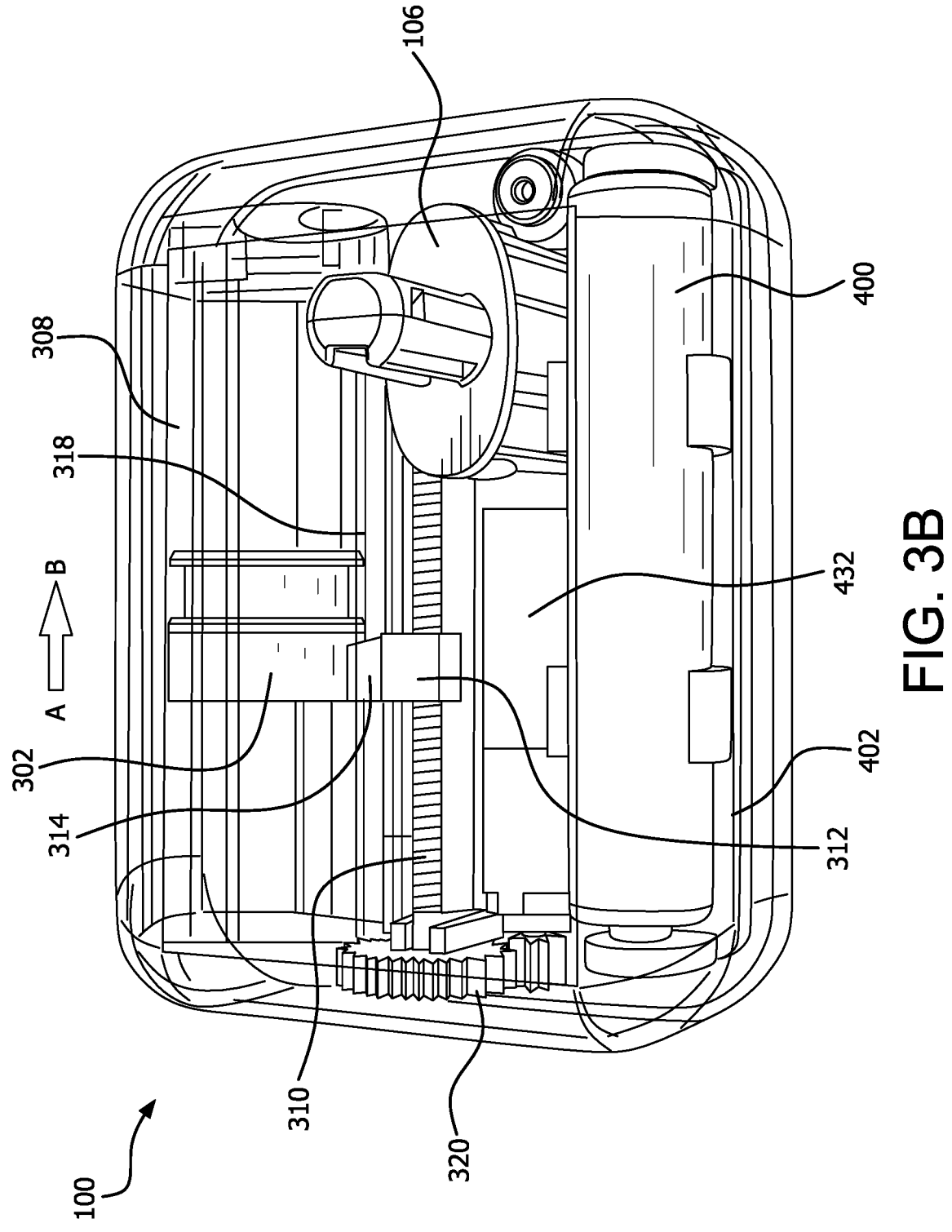
Figure 4:
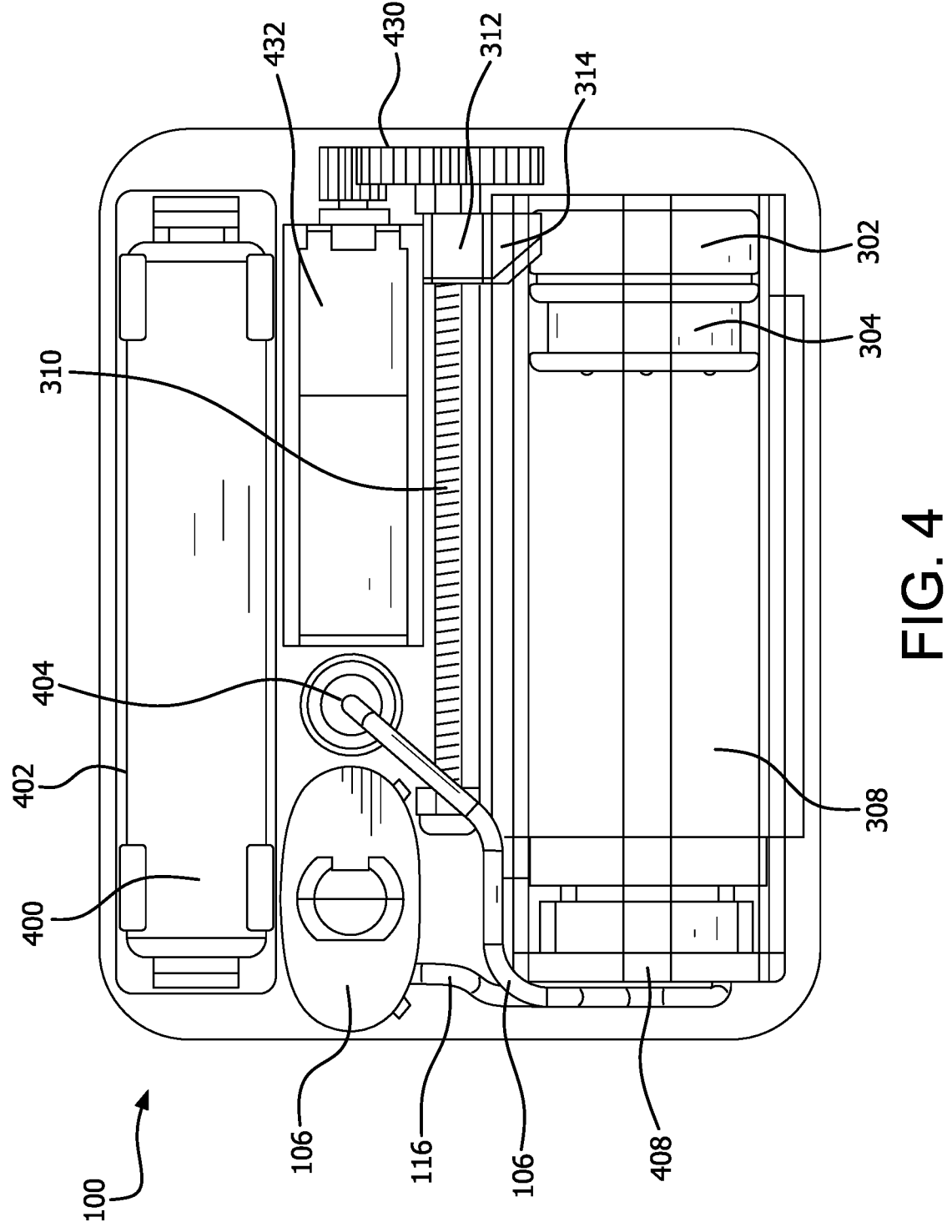
FIG. 4 illustrates a top view of components of a device according to exemplary embodiments of the disclosure.

As diagrammatically shown in the example of FIG. 3A, mechanism 300 can be implemented to function as a screw pump, or a positive displacement pump, which displace fluid or medium with positive pressure from point A to B. Positive displacement pumps driven by gear train 320 that rotates a lead screw 310 parallel to the reservoir 308, which displaces bridge, nut, or threaded cutter 312, which is in threaded communication 311 with lead screw 310, and the pusher 302. In an exemplary configuration, the lead screw 310 is essentially axially parallel to, and extend between proximal and distal portions of, the reservoir 308. The lead screw 310 is in a lateral engagement with the pusher 302 and/or plunger 304. In a further exemplary configuration, blade 314 can be fixed to nut 312 and/or pusher 302 as an interconnect between nut 312 and pusher 302, such that when mechanism 300 drives lead screw 310 to advance nut 312, blade 314 slices through the reservoir 308 and pusher 302 displaces or advances the plunger 304 to create pressure (see also FIG. 8).

Figure 5A:
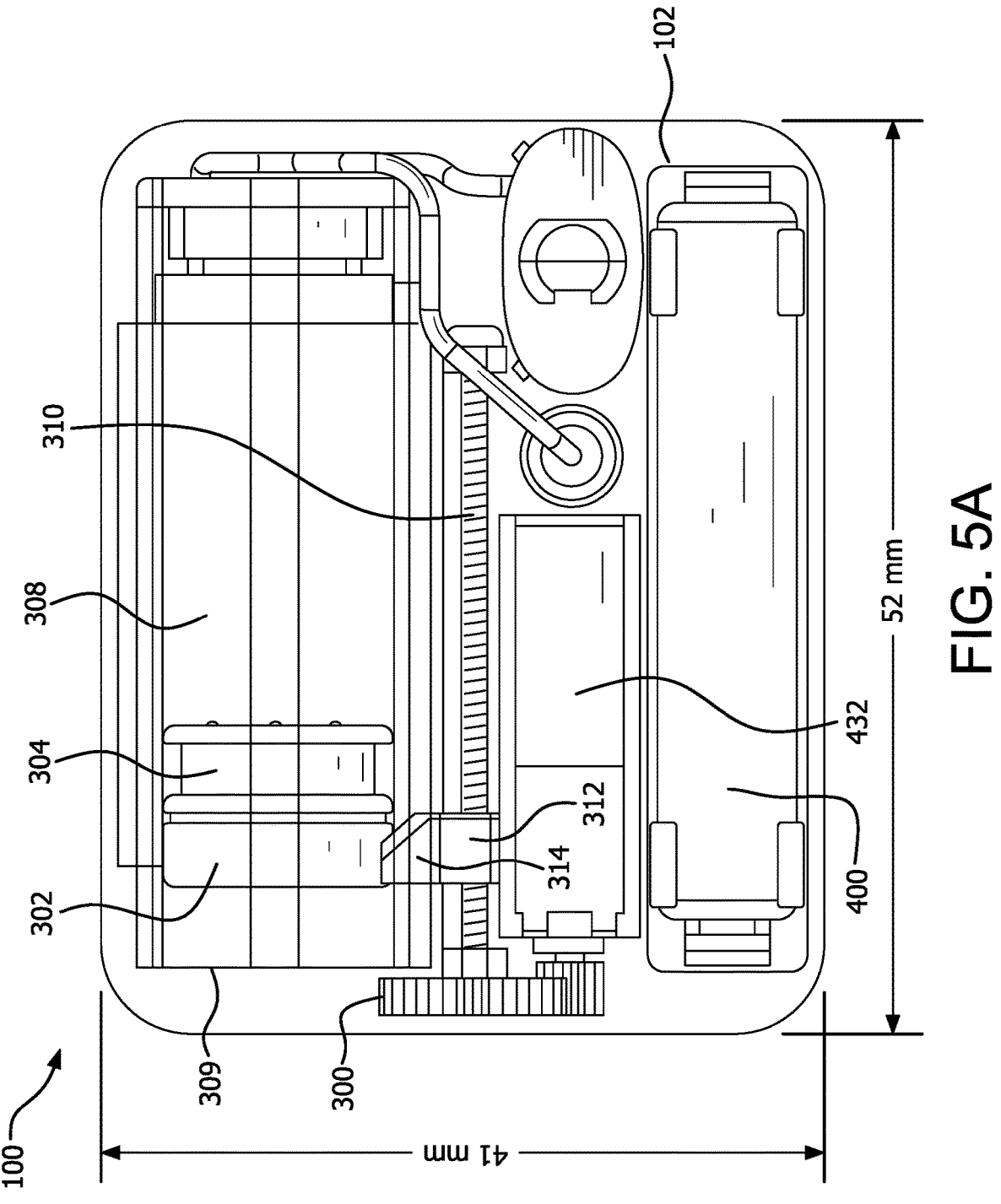
FIGS. 5A and 5B illustrate a top and a side view, respectively of components of a device according to exemplary embodiments of the disclosure.
Figure 5B:
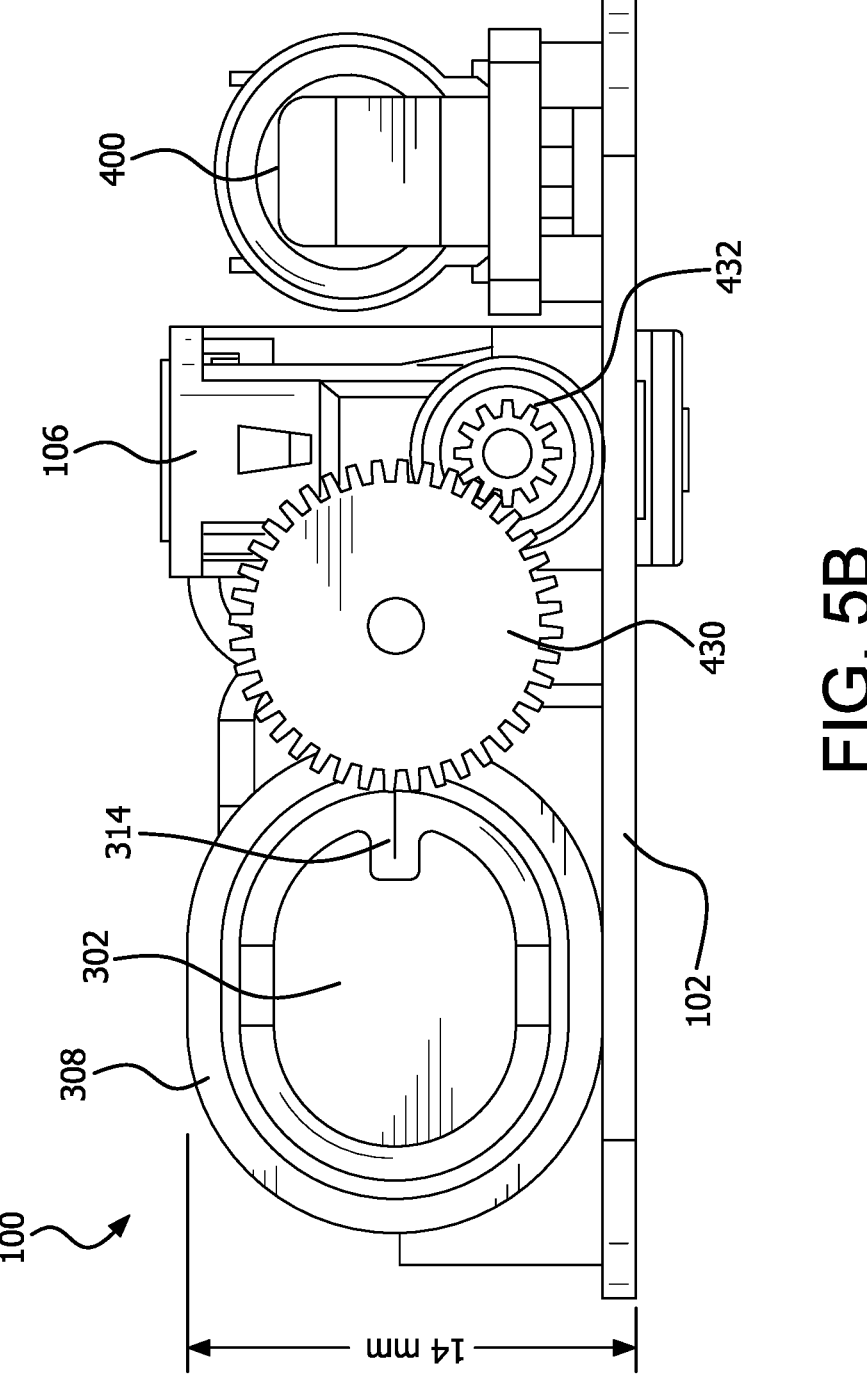
Figure 5C:
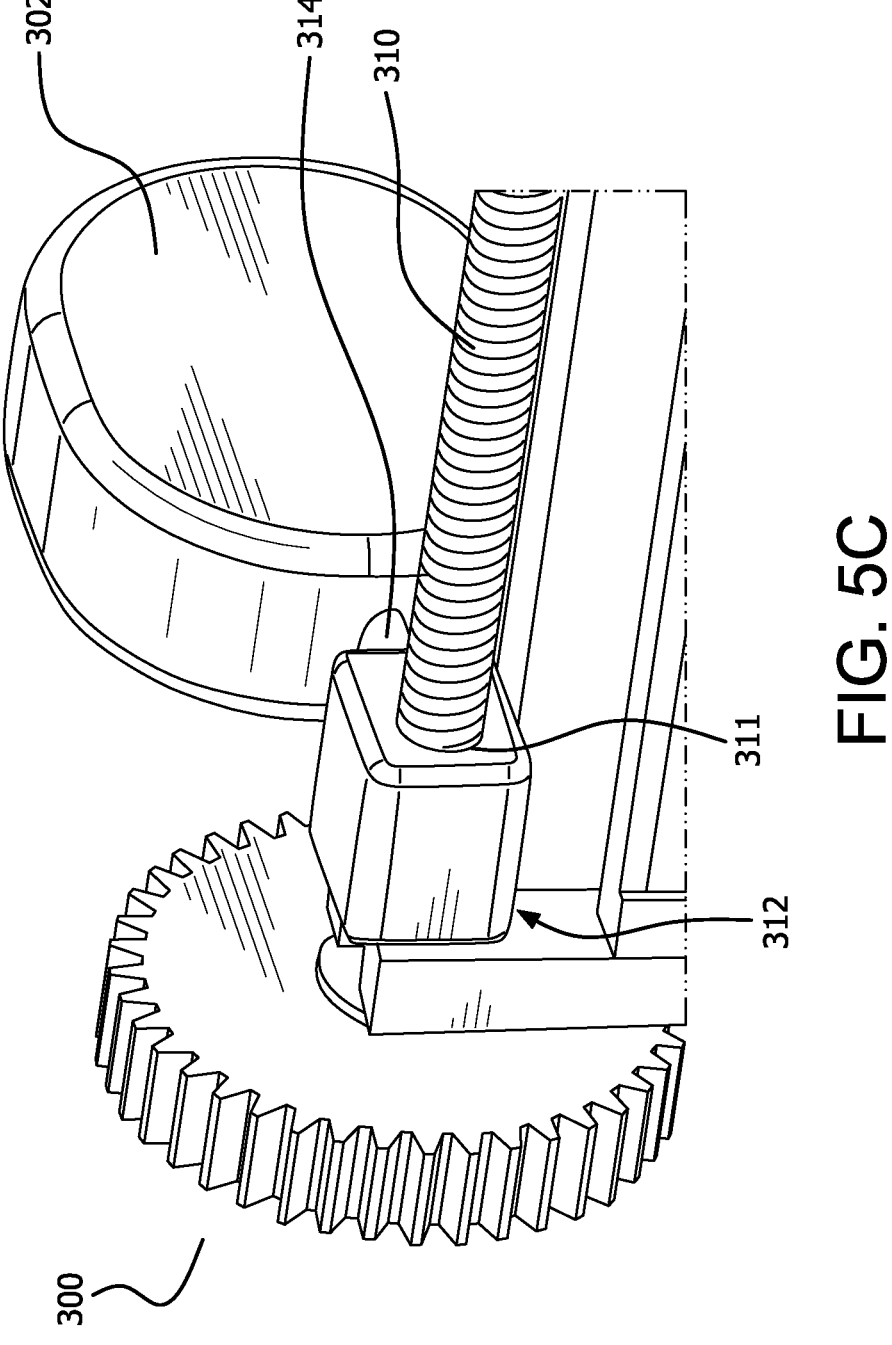
FIG. 5C illustrates a detail of certain components of a device according to exemplary embodiments of the disclosure.
Figure 6A:
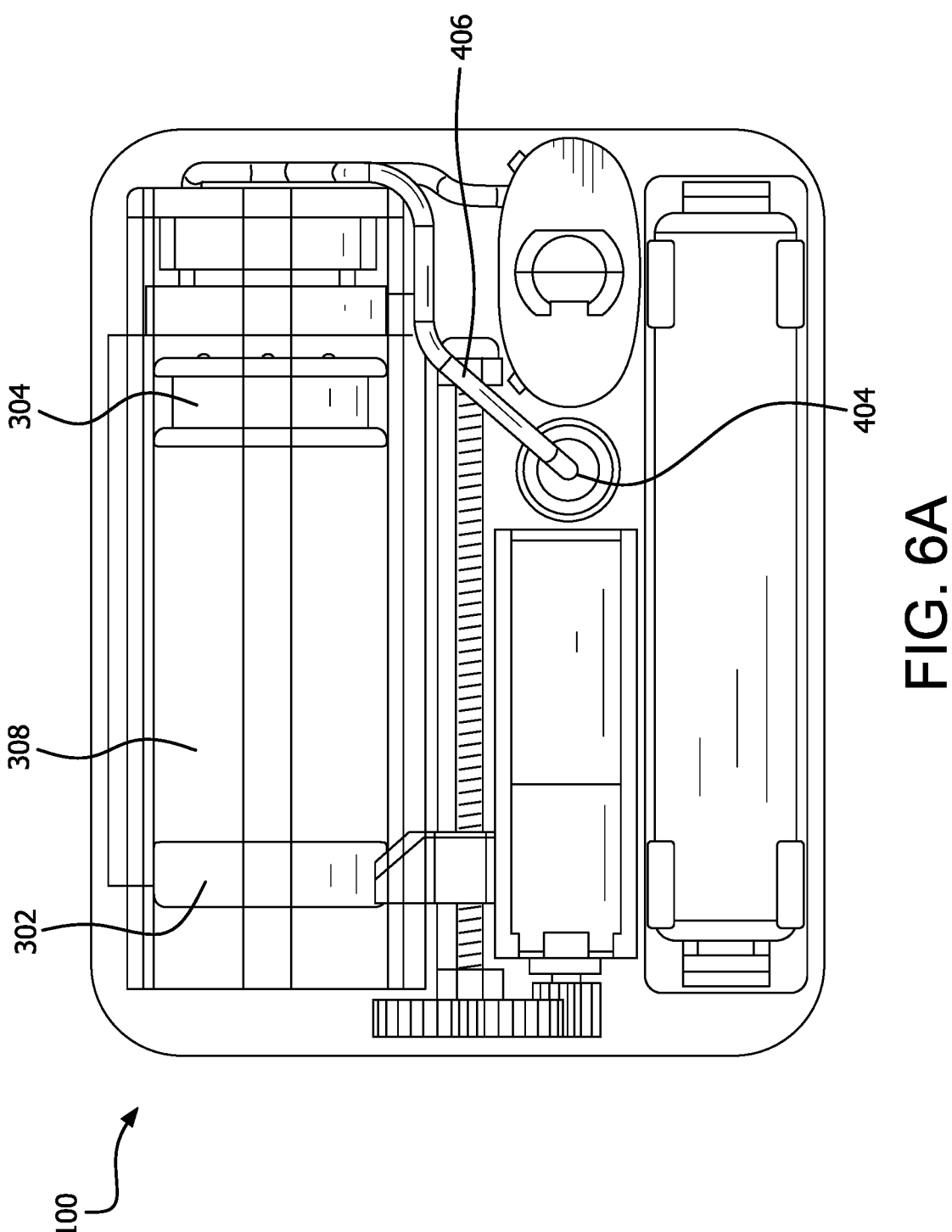
FIGS. 6A and 6B illustrate examples of a top view of components of a device at different stages of operation according to exemplary embodiments of the disclosure.
Figure 6B:
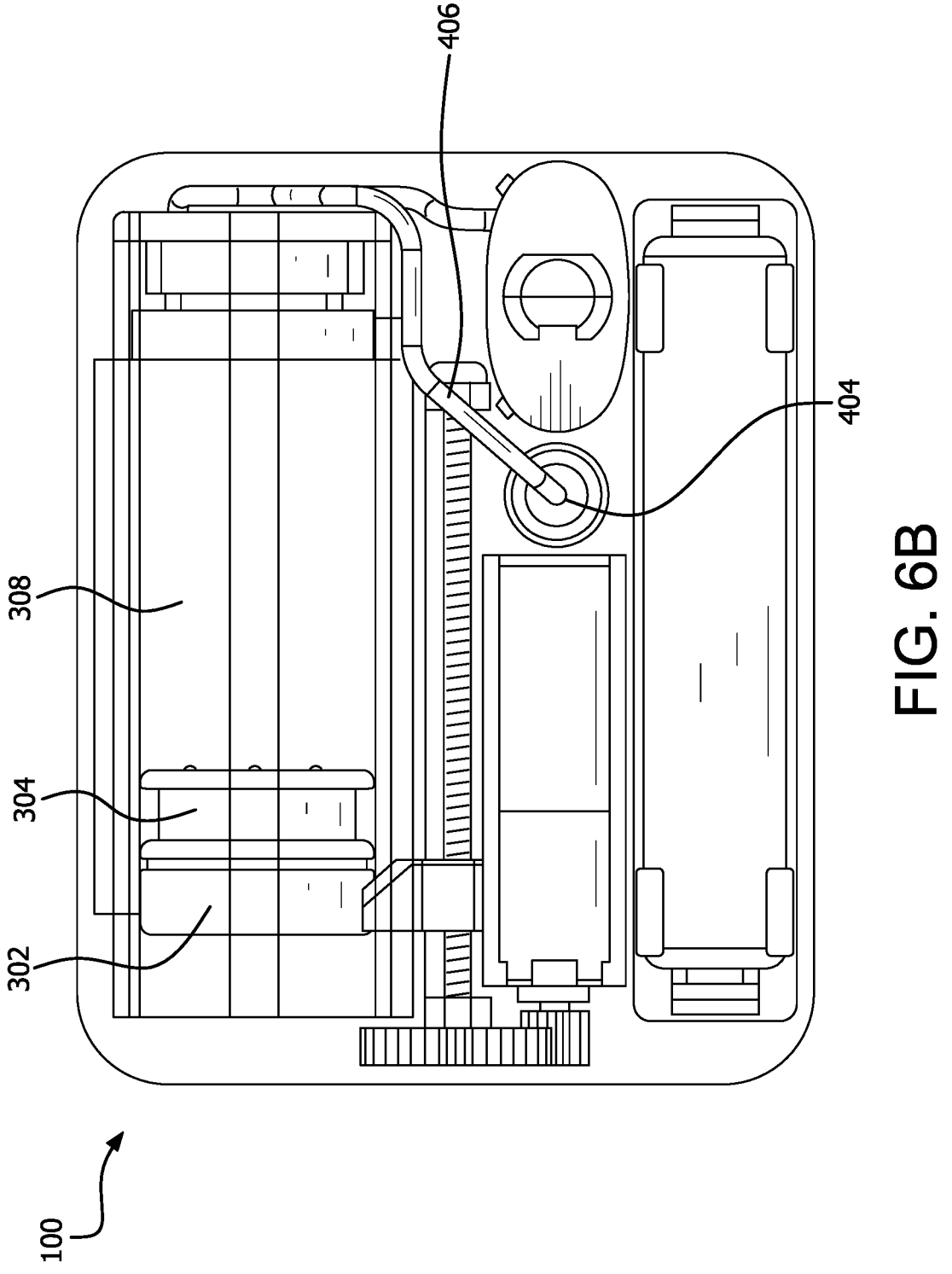

Referring to FIGS. 4, 5A-5C and 6A-6B, in an exemplary implementation of the embodiments of the present disclosure, mechanism 300 includes spur gears 430 driven by a motor 432 connected to a power source such as a battery 400 and controlled by electronics (which may include programmable microprocessors, memory modules, and wire and/or wireless communication modules) disposed on PCB 402. As shown in the example of FIG. 5A (top view of pump 100) and 5B (proximal side view of pump 100), mechanism 300 can be configured with respect to proximal end 309 of reservoir 308 including one or more spur gears 430 in communication with motor 432. FIGS. 5B and 5C also illustrates and example of attachment of blade 314 to pusher 302 (see also FIG. 8A). In addition, FIGS. 5A-SB include examples of exterior dimensions of a patch pump 100 implementing the components according to exemplary embodiments of the disclosure. In a further exemplary implementation, lead screw 310 can have 0-80 thread.

Distal end 307 of reservoir 308 may include an endcap 408 to facilitate connection of reservoir 308 to insertion mechanism 106, for example via tube 116, to dispense medium or fluid out of reservoir 308. Endcap 408 can also be configured to facilitate connection of reservoir 308 to fill port 404, for example via tube 406 to fill reservoir with medium or fluid as diagrammatically shown in FIGS. 6A-6B by displacement of plunger 302 where in FIG. 6A reservoir 308 is empty and in FIG. 6B reservoir 308 is filled, while pusher 304 remains in its initial position and reservoir 308 is intact (not sliced).

Figure 7A:
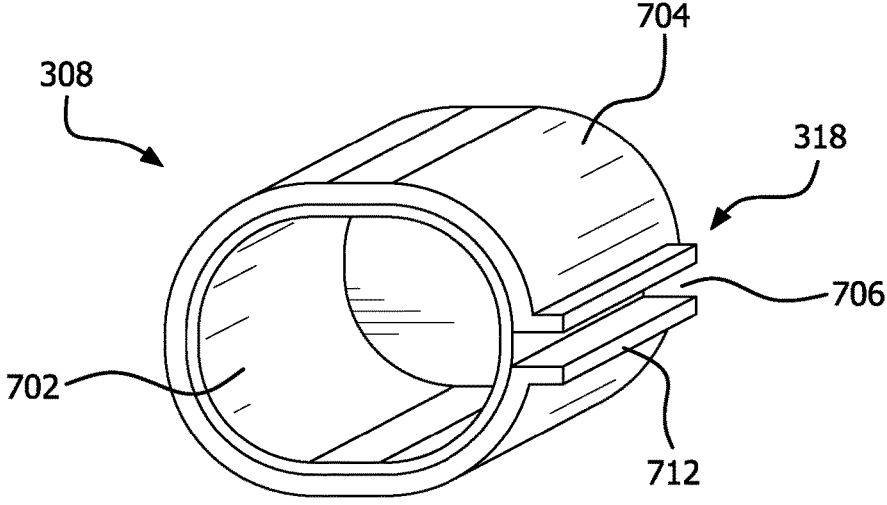
FIGS. 7A, 7B, 7C, 7D and 7E diagrammatically shows perspective, cross sectional, and three-dimensional views of components according to exemplary implementations of embodiments of the disclosure.
Figure 7B:
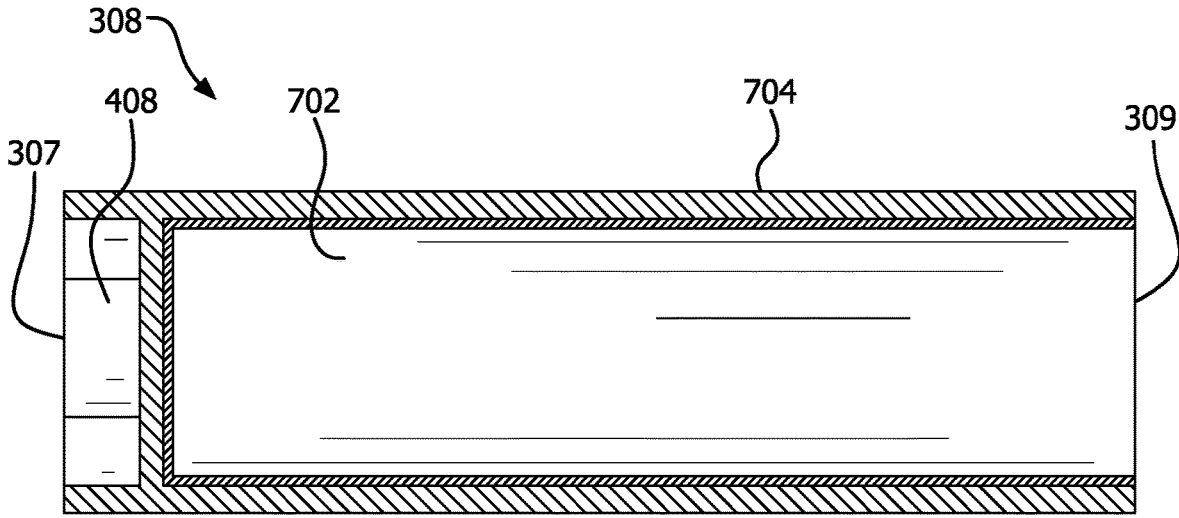
Figure 7C:
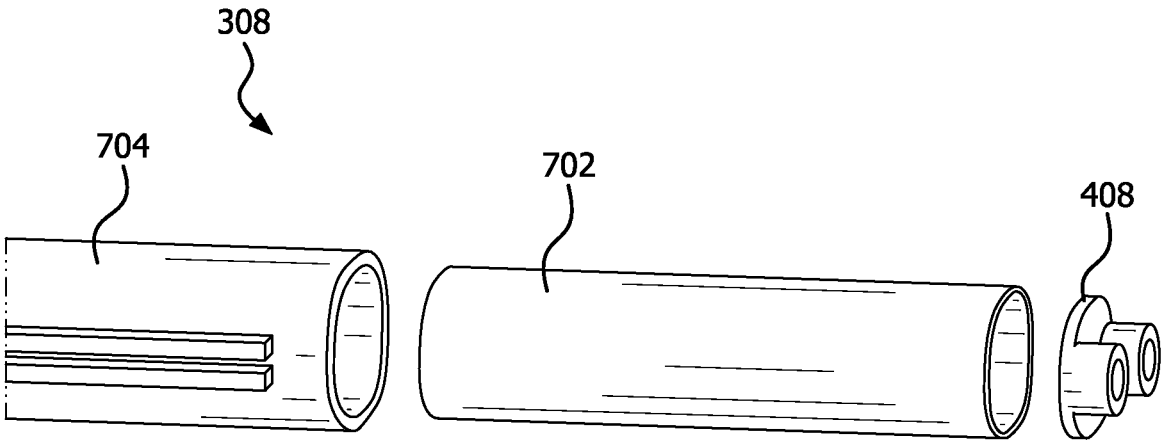
Figure 7D:
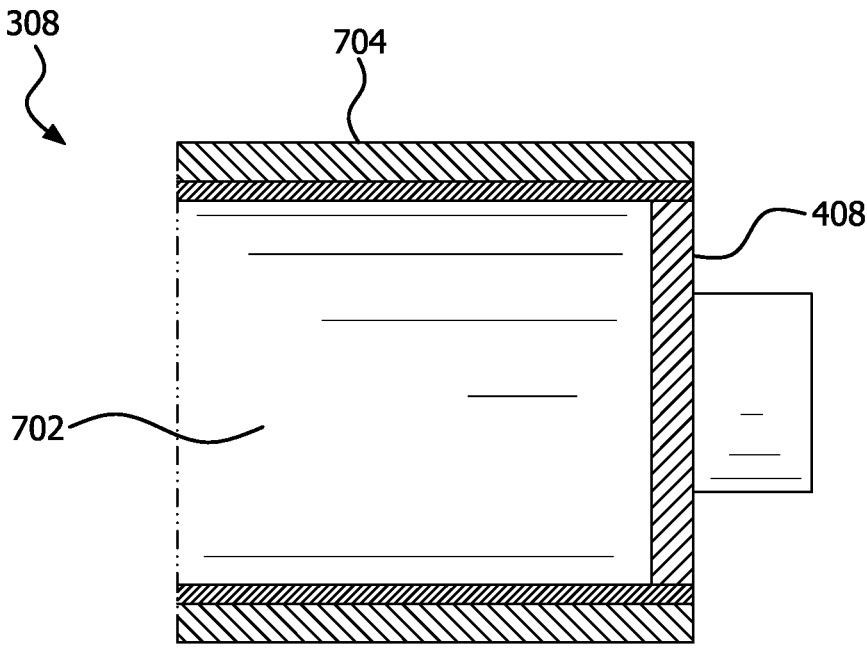
Figure 7E:
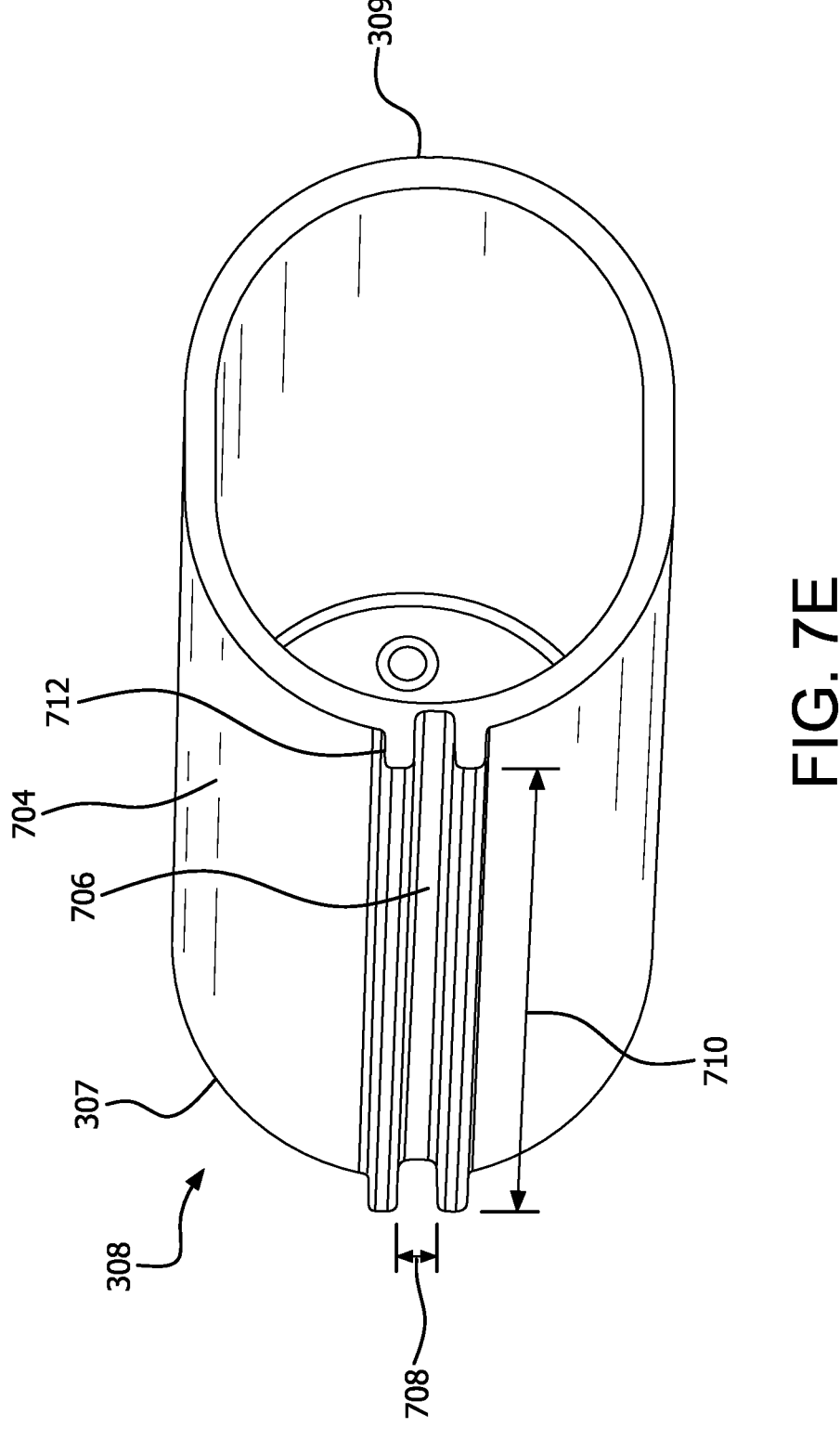

Referring to FIG. 7A-7E In exemplary implementations, reservoir 308 has a sliceable section and/or feature 318 which minimizes cutting force but at the same time doesn't allow pressure loss and crack propagation. In an exemplary implementation, reservoir 308 can include a soft inner layer 702 and a rigid outer layer 704, where the rigid outer layer 704 includes a cutting channel 706 exposing a portion of said soft inner layer 202 therethrough and extending linearly and/or longitudinally between proximal end 309 and distal end 307 of reservoir 308. As shown in FIG. 7E, the width 708 of channel 706 can be configured to accommodate blade 314 and length 710 of channel 706 can be configures based on desired movement of plunger 304 between proximal end 309 and distal end 307 of reservoir 308. Channel 706 can be optionally configured with a feature such as lip(s) 712 to facilitate accurate displacement and or slicing by blade 314 (see, for example, FIG. 8A). FIG. 7B shown an example of an overmolded inner reservoir layer 702 and FIG. 7C show an example of an extruded inner reservoir layer 702. In an exemplary implementation shown in FIG. 7B, end cap 408 can be formed integral with rigid outer layer 704. In an exemplary implementation of FIG. 7C, end cap 408 can be welded and/or bonded to, for example, extrusion as shown in FIG. 7D.

Figure 8A:
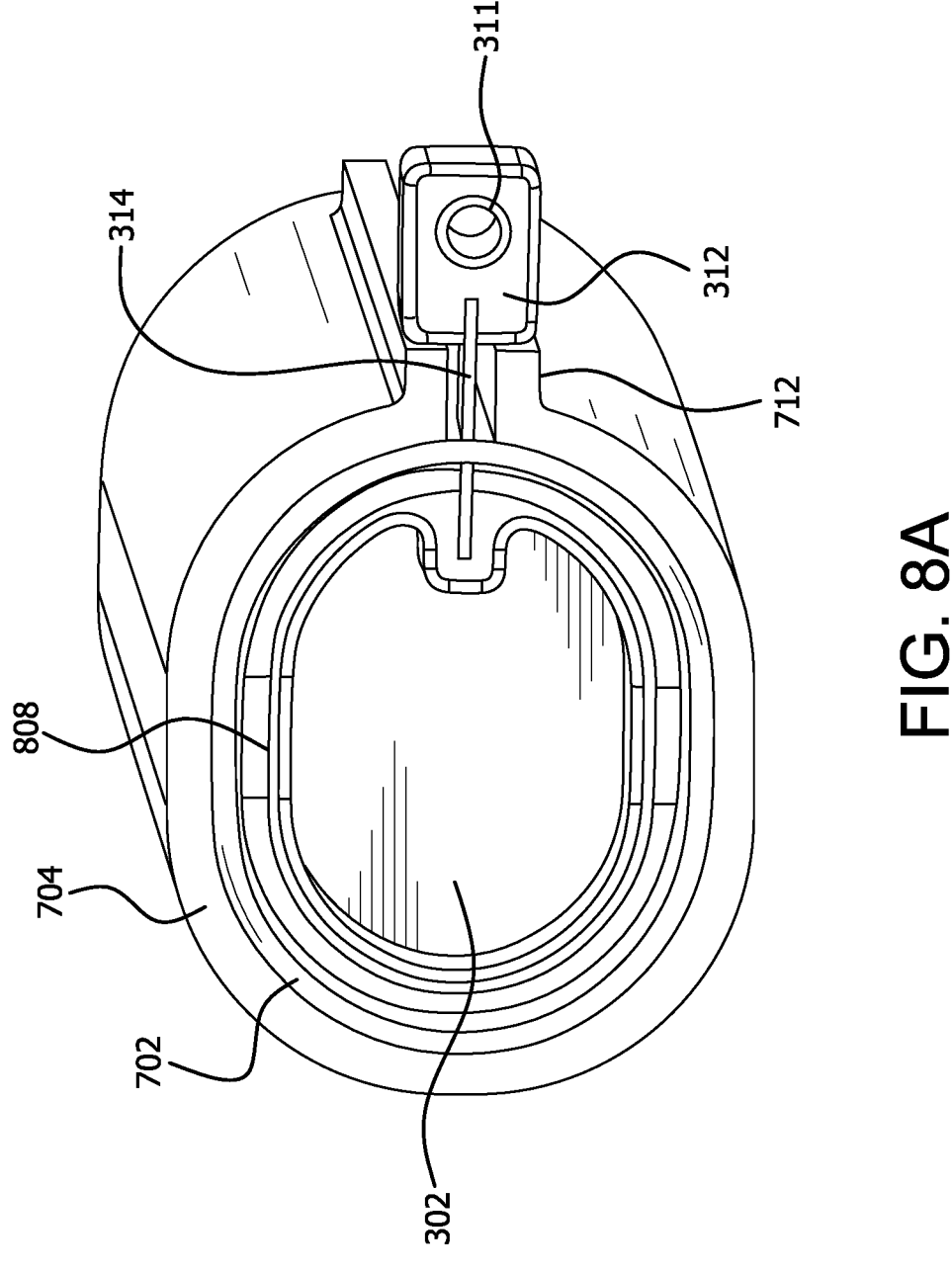
FIGS. 8A and 8B diagrammatically shows perspective and cross sectional views of components according to exemplary implementations of embodiments of the disclosure.
Figure 8B:
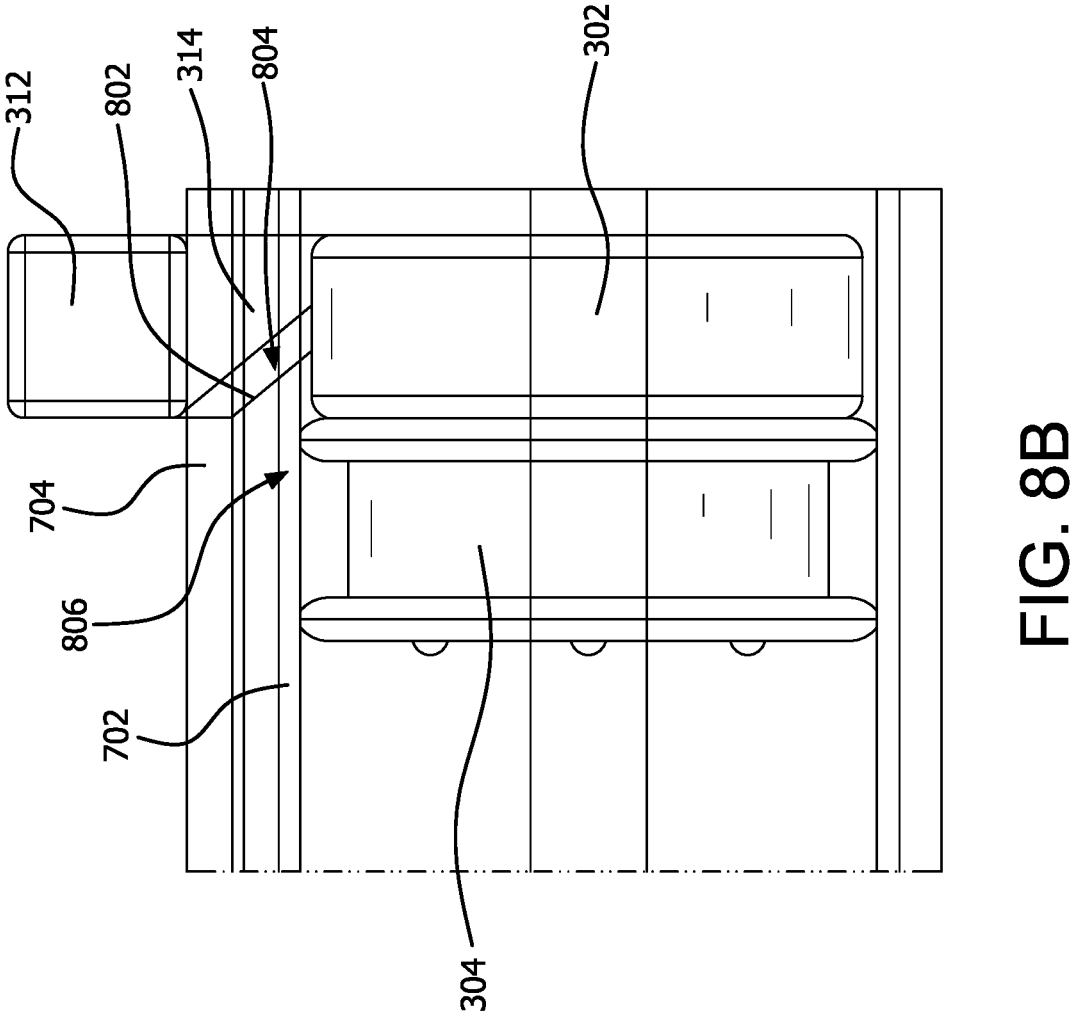

Referring to FIGS. 8A and 8B, in an exemplary implementation a cutting section 802 of blade 314 can be optimized to have least cutting and drag force at cutting location 804 behind plunger seal 806 of plunger 302. In a further exemplary implementation, pusher 304 can include anti rotation features 808 in-place to constrain the rotation transferred from lead screw 310 with minimum energy loss.

While the present disclosure has been shown and described with reference to certain exemplary embodiments thereof, it will be understood by those skilled in the art that various changes in form and details may be made therein without departing from the spirit and scope of the embodiments of the present disclosure. For example, operative variations and alternative different lead designs may be employed to change dosing resolution, encoders may be used to have feedback of drive mechanism, indexing drives can be employed to repeatably and fail-safe advance the plunger. Generally, for example, non-circular syringe barrel cross-sections may be employed to optimize space utilization and tailor device size to best suit user comfort. Furthermore, any of the features or elements of any exemplary implementations of the embodiments of the present disclosure as describes above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of disclosure. The following non-limiting examples of underlying technical principles are applicable and may further facilitate understanding of exemplary implementations of embodiments of the present disclosure: anti-rotation features for a drive nut; friction; gear power transmission; syringe barrel drug container; use of flat cell batteries for space saving; use of a ratchet mechanisms for operational sequencing; single action valves/plugs for connection to insertion mechanism after filling via cable or linkage, and valve/plug either rotated or pulled/pushed to expose patient-side fluid path; concurrent mechanism action; and the like.

Other objects, advantages and salient features of the disclosure will become apparent to those skilled in the art from the details provided, which, taken in conjunction with the annexed drawing figures, disclose exemplary embodiments of the disclosure.

The invention claimed is:

1. A system comprising:
a container for a medium;
a plunger disposed in said container; and
a mechanism for advancing said plunger distally to dispense the medium from said container,
where the mechanism is disposed outside of the container, wherein
said container includes a sliceable portion extending essentially linearly from a proximal portion to a distal portion of said container,
said plunger includes a distal surface disposed inside the container, said distal surface facing said medium inside the container, and
said mechanism comprising:
a pusher acting on said plunger; and
a cutter configured with said pusher behind said plunger, said cutter slices through the sliceable portion of the container as said plunger advances distally to dispense the medium out of the container.

2. The system of claim 1, wherein said mechanism further comprises a lead screw disposed outside of said container and axially fixed with respect to said container, said lead screw being in lateral engagement with said pusher.

3. The system of claim 2, wherein said mechanism further comprises a driver rotating said lead screw to advance said plunger.

4. The system of claim 3, wherein said mechanism comprises at least one gear transferring rotation of said driver to said lead screw, said gear being disposed at a proximal end of said container, said medium being dispensed at a distal end of said container.

5. The system of claim 4, further comprising a nut in threaded communication with said lead screw and connected with at least one of said pusher and said cutter, said nut moving axially relative to said housing container due to rotational movement of said lead screw, thereby advancing said pusher and said cutter.

6. The system of claim 2, further comprising a nut in threaded communication with said lead screw and connected with at least one of said pusher and said cutter, said nut moving axially relative to said container due to rotational movement of said lead screw, thereby advancing said pusher and said cutter.

7. The system of claim 5, wherein said cutter comprises a blade, said blade laterally connecting said pusher and said nut, said blade comprising a slicing edge that slices through said sliceable portion of said container.

8. The system of claim 7, wherein
said container comprises:
a soft inner layer accommodating said medium;
a rigid outer layer; and
said sliceable portion comprises a cutting channel exposing a portion of said soft inner layer and extending linearly between a proximal end and a distal end of said container.

9. The system of claim 1, wherein said container comprises an endcap disposed at a distal end portion of said container, said endcap comprising at least one of an outlet for dispensing said medium and an inlet for filling said container.

10. The system of claim 1, wherein
said container comprises:
a soft inner layer accommodating said medium;
a rigid outer layer; and
said sliceable portion comprises a cutting channel exposing a portion of said soft inner layer and extending linearly between a proximal end and a distal end of said container.

11. The system of claim 10, wherein said cutting channel is configured to accommodate said cutter when said plunger advances to dispense said medium, said cutter advancing through said channel slicing said exposed portion of said soft inner layer.

12. The system of claim 10, wherein said soft inner layer comprises an overmold inside said rigid outer layer.

13. The system of claim 10, wherein said soft inner layer is bonded inside said rigid outer layer.

14. The system of claim 13, wherein said container is cylindrical having one of a circular or elliptical cross section, an outer wall of said inner layer extending parallel to an inner wall of said outer layer.

15. The system of claim 10, wherein said container is cylindrical having one of a circular or elliptical cross section, an outer wall of said inner layer extending parallel to an inner wall of said outer layer.

16. The system of claim 1, wherein said container is cylindrical having one of a circular or elliptical cross section.

17. A patch pump comprising a base an outer housing and the system as claimed in claim 1 disposed on said base.

18. A medicament delivery device comprising an insertion mechanism and the system as claimed in claim 1, wherein the insertion mechanism is connected to said container.

* * * * *